United States Patent
Blanchard

(10) Patent No.: US 11,034,927 B2
(45) Date of Patent: Jun. 15, 2021

(54) CELL CULTURE INCUBATORS WITH INTEGRATED IMAGING SYSTEMS

(71) Applicant: Thrive Bioscience, Inc., Wakefield, MA (US)

(72) Inventor: Alan Blanchard, Middleton, MA (US)

(73) Assignee: Thrive Bioscience, Inc., Wakefield, MA (US)

(*) Notice: Subject to any disclaimer, the term of this patent is extended or adjusted under 35 U.S.C. 154(b) by 0 days.

(21) Appl. No.: 15/563,375

(22) PCT Filed: Mar. 31, 2016

(86) PCT No.: PCT/US2016/025349
§ 371 (c)(1),
(2) Date: Sep. 29, 2017

(87) PCT Pub. No.: WO2016/161163
PCT Pub. Date: Oct. 6, 2016

(65) Prior Publication Data
US 2018/0346868 A1   Dec. 6, 2018

Related U.S. Application Data

(60) Provisional application No. 62/141,187, filed on Mar. 31, 2015.

(51) Int. Cl.
| | | |
|---|---|---|
| C12M 1/34 | (2006.01) | |
| C12M 1/00 | (2006.01) | |
| C12M 1/36 | (2006.01) | |
| G02B 21/00 | (2006.01) | |
| G03H 1/00 | (2006.01) | |
| C12M 1/32 | (2006.01) | |

(52) U.S. Cl.
CPC ............ *C12M 41/36* (2013.01); *C12M 23/50* (2013.01); *C12M 41/14* (2013.01); *C12M 41/46* (2013.01); *C12M 41/48* (2013.01); *C12M 23/12* (2013.01)

(58) Field of Classification Search
CPC .................................................. C12M 41/36
USPC .................................................. 435/303.1
See application file for complete search history.

(56) References Cited

U.S. PATENT DOCUMENTS

| 8,548,745 B2 | 10/2013 | Callahan et al. |
| 2003/0040104 A1* | 2/2003 | Barbera-Guillem ........................ C12M 23/24 435/286.2 |
| 2004/0029266 A1 | 2/2004 | Barbera-Guillem |

(Continued)

FOREIGN PATENT DOCUMENTS

| CN | 101313196 A | 11/2008 |
| CN | 101501180 A | 8/2009 |

(Continued)

OTHER PUBLICATIONS

International Search Report and Written Opinion for Application No. PCT/US2016/025349 dated Oct. 6, 2016.

(Continued)

*Primary Examiner* — Holly Kipouros
(74) *Attorney, Agent, or Firm* — Wolf, Greenfield & Sacks, P.C.

(57) ABSTRACT

Aspects relate to automated cell culture incubators comprising imaging systems, e.g., holographic or phase-contrast imagers, configured for imaging said cells within the incubators.

8 Claims, 3 Drawing Sheets

(56) References Cited

U.S. PATENT DOCUMENTS

| | | | |
|---|---|---|---|
| 2005/0239040 A1* | 10/2005 | Lindenberg | C12M 21/06 |
| | | | 435/2 |
| 2010/0099177 A1 | 4/2010 | Yang et al. | |
| 2013/0074614 A1 | 3/2013 | Holmes et al. | |
| 2013/0210130 A1* | 8/2013 | Larcher | C12M 23/44 |
| | | | 435/288.7 |
| 2014/0106386 A1* | 4/2014 | Umeno | G01N 35/0099 |
| | | | 435/23 |
| 2014/0273191 A1 | 9/2014 | Tipgunlakant et al. | |
| 2015/0079621 A1 | 3/2015 | An et al. | |
| 2015/0278625 A1* | 10/2015 | Finkbeiner | G02B 27/32 |
| | | | 348/79 |

FOREIGN PATENT DOCUMENTS

| | | | |
|---|---|---|---|
| CN | 102471744 A | | 5/2012 |
| CN | 104245917 A | | 12/2014 |
| EP | 1 553 166 A1 | | 7/2005 |
| JP | H02-171866 A | | 7/1990 |
| JP | 2009-511998 A | | 3/2009 |
| WO | PCT/EP1997/006721 | * | 11/1998 |
| WO | WO 2011/010449 A1 | | 1/2011 |

OTHER PUBLICATIONS

International Preliminary Report on Patentability for Application No. PCT/US2016/025349 dated Oct. 12, 2017.
Extended European Search Report in connection with Application No. EP 16774234.5 dated Nov. 5, 2019.
EP 16774234.5, Nov. 5, 2019, Extended European Search Report.

\* cited by examiner

CELL CULTURE INCUBATORS WITH INTEGRATED IMAGING SYSTEMS

RELATED APPLICATIONS

This Application is a National Stage filing under 35 U.S.C. § 371 of International Appliation No. PCT/US2016/025349, filed on Mar. 31, 2016. International Application No. PCT/US2016/025349 claims the benefit under 35 U.S.C. 119(e) of U.S. provisional application U.S. Ser. No. 62/141,187, filed Mar. 31, 2015 and entitled "Cell Culture Incubators With Integrated Imaging Systems", the entire contents of which are incorporated by reference herein.

FIELD

Aspects relate to cell culture incubators and to methods for using such incubators.

BACKGROUND

Cell culture is a useful technique in both research and clinical contexts. However, maintenance of cell cultures (e.g. long term cultures, tissue preparations, in vitro fertilization preparations, etc.) in presently available cell incubators is a laborious process requiring highly trained personnel and stringent aseptic conditions. This high level of human involvement can introduce contaminants into the culture, thereby lowering culture efficiency. Furthermore, there is often a need to monitor cell growth, viability and/or health in long term cultures, which is a challenge to accomplish non-invasively and effectively with conventional incubators. Accordingly, new types of cell culture incubators that provide long-term culture system with minimal human involvement are needed.

SUMMARY

This document provides cell culture incubators having integrated imaging devices. In some embodiments, holographic microscopic imagers are provided herein that are able to non-invasively quantify and visualize biological cells or tissues within an incubator during cell culture. In some embodiments, this document provides cell culture incubators having phase-contrast imagers (e.g., phase contrast microscope).

This document relates to cell culture incubators that include an incubator cabinet having an internal chamber for incubation of cells in one or more cell culture vessels, and one or more imagers (e.g., a holographic imager) configured for imaging the cells within the internal chamber. In some embodiments, the holographic imager includes a first imaging location. In some embodiments, the internal chamber is configured to hold the one or more cell culture vessels (e.g., flasks, suspension culture flasks, spinner flasks, plates, petri dishes, and bags) and/or other items (e.g., one or more supplies such as disposable supplies required for cell manipulation, for example, pipette tips). In some embodiments, the incubator can include an external door opening from an external environment to the internal chamber. In some embodiments, a storage location is provided within the internal chamber for storing the one or more cell culture vessels. In some embodiments the incubator can include, a cell culture vessel transfer device for moving the one or more cell culture vessels from the first imaging location to the storage location or from the storage location to the first imaging location. In certain embodiments, the holographic imager is a holographic microscope. In some embodiments, the cell culture vessel transfer device includes one or more robotic elements. In certain embodiments, the incubator further includes a controller of the cell culture vessel transfer device. In some embodiments, the controller is located exterior to the incubator cabinet. In certain embodiments, the controller includes a computer. In some embodiments, the one or more cell culture vessels have one or more fiducial marks for facilitating alignment of the one or more cell culture vessels with the holographic imager.

In some embodiments, the incubator further comprises a second imager comprising a second imaging location, the second imager configured for imaging the cells within the internal chamber when the one or more cell culture vessels are at the second imaging location. In some embodiments, the second imager is a microscope. In certain embodiments, the cell culture vessel transfer device is configured to move the one or more cell culture vessels from the first imaging location to the second imaging location or from the second imaging location to the first imaging location. In some embodiments, when the one or more cell culture vessels are moved from the first imaging location to the second imaging location or from the second imaging location to the first imaging location, an imaging field at the first imaging location and an imaging field at the second imaging location are substantially aligned.

Aspects of this document relate to cell culture incubators that include an incubator cabinet having an internal chamber for incubation of cells in one or more cell culture vessels, in which the internal chamber is configured to hold the one or more cell culture vessels, and further include a holographic imager and a second imager, in which the holographic imager and the second imager are configured for imaging the cells within the internal chamber when the one or more cell culture vessels are at an imaging location. In some embodiments the incubator can include, a cell culture vessel transfer device for moving the one or more cell culture vessels within the internal chamber (e.g., between the two imagers). In some embodiments, a storage location is provided within the internal chamber for storing the one or more cell culture vessels. In some embodiments, the holographic imager is a holographic microscope. In some embodiments, the imaging field of the holographic imager and the imaging field of the second imager are substantially aligned. In some embodiments, the incubator further includes a location at which one or more cell culture vessels can be maintained. In some embodiments, the cell culture vessel transfer device is configured to move the one or more cell culture vessels between the imaging location, the maintenance location, and the storage location. In some embodiments, the incubator further includes a controller of the cell culture vessel transfer device. In certain embodiments, the controller is located exterior to the incubator cabinet. In some embodiments, the controller includes a computer.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. Various embodiments of the invention will now be described, by way of example, with reference to the accompanying drawings, in which.

DETAILED DESCRIPTION

Figure 1:
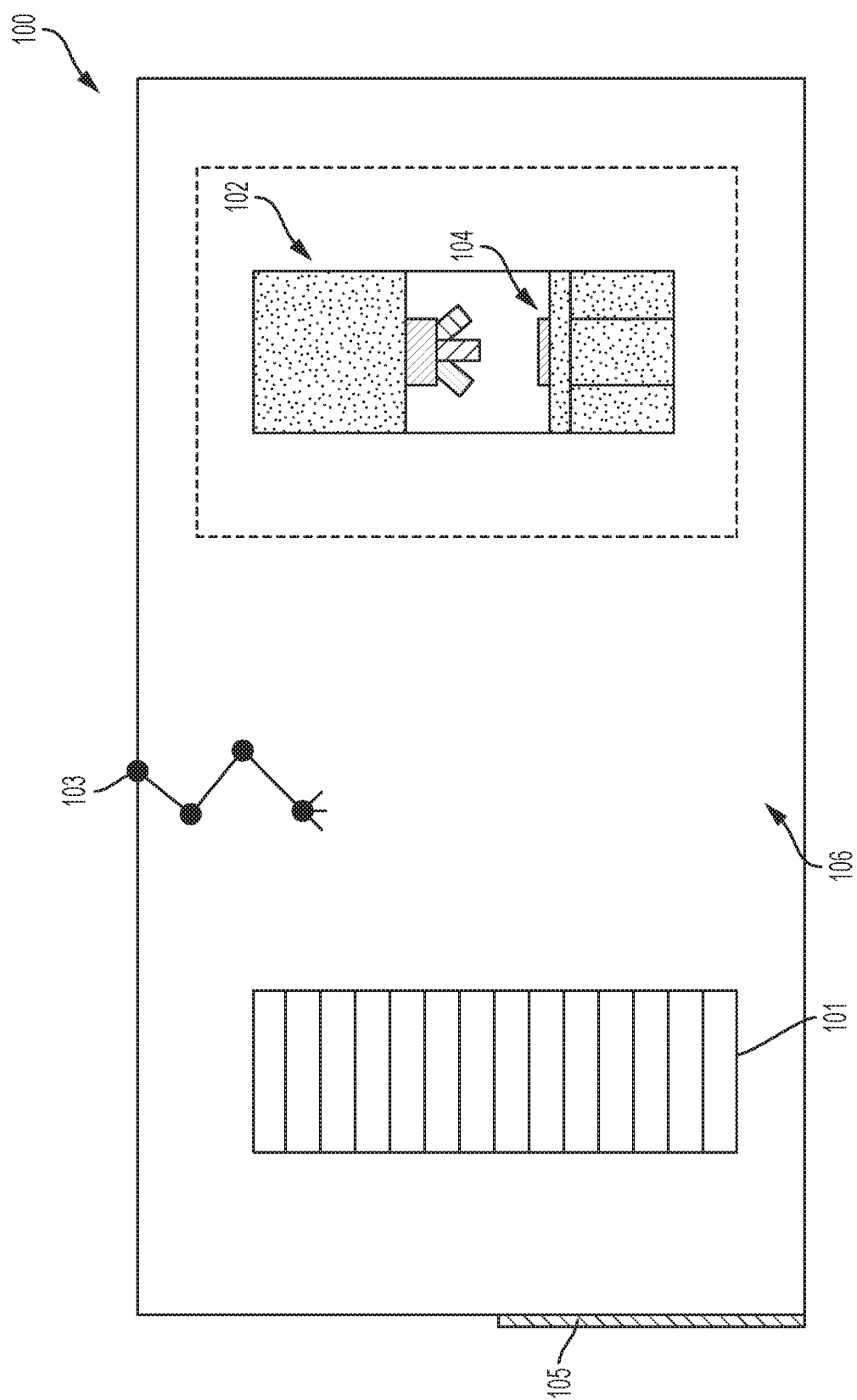
FIG. 1 is a schematic of an automated cell culture incubator having an integrated imaging system.

According to some aspects, this document provides cell culture incubators having integrated imaging devices. In particular, holographic microscopic imagers are provided herein that are able to non-invasively quantify and visualize biological cells or tissues within an automated incubator during cell culture. Certain aspects of this document relate to incubators and methods for culturing, manipulating, and/or monitoring cells under controlled conditions (e.g., under aseptic and/or sterile conditions) that permit monitoring and analysis of cells in a sterile environment by microscopy. In some aspects, incubators and methods include automated components. In some aspects, incubators and methods are useful for long term cell culture (e.g., to grow and maintain cells for recombinant protein expression or to grow and/or differentiate cells for therapeutic applications such as implantation). In some embodiments, cell cultures are grown within a culture vessel in an incubator provided herein.

According to one aspect, the cell culture incubator includes an incubator cabinet with an imaging location and a storage location. In some embodiments, the imaging location and the storage location are two distinct locations within the incubator cabinet. The incubator may include a transfer device that moves cell culture vessels between the imaging location and the storage location. In other embodiments, the imaging location and the storage location are the same, such that the cell culture vessels are imaged at the storage location.

The imaging location is the location where an imager images one or more cells. For example, an imaging location may be disposed above a light source and/or in vertical alignment with one or more optical elements (e.g., lens, apertures, mirrors, objectives, and light collectors).

The storage location may be configured to store a plurality of cell culture vessels. For example, a storage location may include one or more storage arrays, racks, shelves, pigeonholes, cubbies, trays, slots, or other positions or mechanisms. In some embodiments, a storage location may be configured to store cell culture vessels horizontally, while in other embodiments a storage location may be configured to store cell culture vessels vertically. For example, a storage location may include a plurality of slots to receive cell culture vessels stacked vertically over one another. A storage location may be configured to hold 1, 2, 3, 4, 5, 6, 7, 8, 9, 10, 15, 20, 25, 30, 35, 40, 45, 50, 100, or any other number of cell culture vessels. In some embodiments, a storage location may be configured to hold greater than 100 cell culture vessels.

A storage location may be configured to securely hold or receive one or more cell culture vessels. For example, one or more components of the storage location may include one or more locking mechanisms that have one or more adhesive, magnetic, electrical, and/or mechanical components (e.g., snaps, fasteners, locks, clasps, gaskets, o-rings, septa, springs, and other engagement members). In some embodiments, a storage location and/or cell culture vessel may include one or more grooves or depressions and/or may involve pieces of molded plastic. For example, a cell culture vessel may include one or more protruded features (e.g., a rim or knob) that are molded for insertion into one or more corresponding grooves, holes, or depressions at a storage location. In some cases, a cell culture vessel may include one or more grooves, holes, or depressions that are molded to fit one or more corresponding protruded features at a storage location.

The cell culture incubator may include one or more imagers to image cells. In some embodiments, incubator cabinets provided herein are configured with a microscope or other imager for purposes of monitoring cell growth, viability or other aspect of cells. In some embodiments, the microscope or imager is used in conjunction with an assay performed within the incubator cabinet, such as an image based phenotypic screen or assay. In certain embodiments, an imager includes one or more lenses, fibers, cameras (e.g., a charge-coupled device camera), apertures, mirrors, light sources (e.g., a laser or lamp), or other optical elements. An imager may be a microscope. In some embodiments, the imager is a bright-field microscope. In other embodiments, the imager is a holographic imager or microscope. In other embodiments the imager is a phase-contrast microscope. In other embodiments, the imager is a fluorescence imager or microscope.

As used herein, the fluorescence imager is an imager which is able to detect light emitted from fluorescent markers present either within or on the surface of cells or other biological entities, said markers emitting light in a specific wavelength when absorbing a light of different specific excitation wavelength.

As used herein, a "bright-field microscope" is an imager that illuminates a sample and produces an image based on the light absorbed by the sample. Any appropriate bright-field microscope may be used in combination with an incubator provided herein.

As used herein, a "phase-contrast microscope" is an imager that converts phase shifts in light passing through a transparent specimen to brightness changes in the image. Phase shifts themselves are invisible, but become visible when shown as brightness variations. Any appropriate phase-contrast microscope may be used in combination with an incubator provided herein.

As used herein, a "holographic imager" is an imager that provides information about an object (e.g., sample) by measuring both intensity and phase information of electromagnetic radiation (e.g., a wave front). For example, a holographic microscope measures both the light transmitted after passing through a sample as well as the interference pattern (e.g., phase information) obtained by combining the beam of light transmitted through the sample with a reference beam.

A holographic imager may also be a device that records, via one or more radiation detectors, the pattern of electromagnetic radiation, from a substantially coherent source, diffracted or scattered directly by the objects to be imaged, without interfering with a separate reference beam and with or without any refractive or reflective optical elements between the substantially coherent source and the radiation detector(s).

In some embodiments, an incubator cabinet includes a single imager. In some embodiments, an incubator cabinet includes two imagers. In some embodiments, the two imagers are the same type of imager (e.g., two holographic imagers, two phase-contrast microscopes or two bright-field microscopes). In some embodiments, the first imager is a bright-field microscope and the second imager is a holographic imager. In some embodiments, the first imager is a phase-contrast microscope and the second imager is a holographic imager. In some embodiments, the first imager is a phase-contrast microscope and the second imager is a bright-field microscope. In some embodiments, an incubator cabinet comprises more than 2 imagers. In some embodiments, cell culture incubators comprise three imagers. In some embodiments, cell culture incubators having 3 imagers comprise a holographic microscope, a bright-field microscope, and a fluorescence microscope. In some embodiments, cell culture incubators having 3 imagers comprise a holographic microscope, a phase-contrast microscope, and a fluorescence microscope.

As used herein, an "imaging location" is the location where an imager images one or more cells. For example, an imaging location may be disposed above a light source and/or in vertical alignment with one or more optical elements (e.g., lens, apertures, mirrors, objectives, and light collectors).

Holographic Microscopy

In some embodiments, holographic microscopy is used to obtain images (e.g., a collection of three-dimensional microscopic images) of cells for analysis (e.g., cell counting) during culture (e.g., long-term culture) in an incubator (e.g., within an internal chamber of an incubator as described herein). In some embodiments, a holographic image is created by using a light field, from a light source scattered off objects, which is recorded and reconstructed. In some embodiments, the reconstructed image can be analyzed for a myriad of features relating to the objects. In some embodiments, methods provided herein involve holographic interferometric metrology techniques that allow for non-invasive, marker-free, quick, full-field analysis of cells, generating a high resolution, multi-focus, three-dimensional representation of living cells in real time.

In some embodiments, holography involves shining a coherent light beam through a beam splitter, which divides the light into two equal beams: a reference beam and an illumination beam. In some embodiments, the reference beam, often with the use of a mirror, is redirected to shine directly into the recording device without contacting the object to be viewed. In some embodiments, the illumination beam is also directed, using mirrors, so that it illuminates the object, causing the light to scatter. In some embodiments, some of the scattered light is then reflected onto the recording device. In some embodiments, a laser is generally used as the light source because it has a fixed wavelength and can be precisely controlled. In some embodiments, to obtain clear images, holographic microscopy is often conducted in the dark or in low light of a different wavelength than that of the laser in order to prevent any interference. In some embodiments, the two beams reach the recording device, where they intersect and interfere with one another. In some embodiments, the interference pattern is recorded and is later used to reconstruct the original image. In some embodiments, the resulting image can be examined from a range of different angles, as if it was still present, allowing for greater analysis and information attainment.

In some embodiments, digital holographic microscopy is used in incubators described herein. In some embodiments, digital holographic microscopy light wave front information from an object is digitally recorded as a hologram, which is then analyzed by a computer with a numerical reconstruction algorithm. In some embodiments, the computer algorithm replaces an image forming lens of traditional microscopy. The object wave front is created by the object's illumination by the object beam. In some embodiments, a microscope objective collects the object wave front, where the two wave fronts interfere with one another, creating the hologram. Then, the digitally recorded hologram is transferred via an interface (e.g., IEEE1394, Ethernet, serial) to a PC-based numerical reconstruction algorithm, which results in a viewable image of the object in any plane.

In some embodiments, in order to procure digital holographic microscopic images, specific materials are utilized. In some embodiments, an illumination source, generally a laser, is used as described herein. In some embodiments, a Michelson interferometer is used for reflective objects. In some embodiments, a Mach-Zehnder interferometer for transmissive objects is used. In some embodiments, interferometers can include different apertures, attenuators, and polarization optics in order to control the reference and object intensity ratio. In some embodiments, an image is then captured by a digital camera, which digitizes the holographic interference pattern. In some embodiments, pixel size is an important parameter to manage because pixel size influences image resolution. In some embodiments, an interference pattern is digitized by a camera and then sent to a computer as a two-dimensional array of integers with 8-bit or higher grayscale resolution. In some embodiments, a computer's reconstruction algorithm then computes the holographic images, in addition to pre- and post-processing of the images.

Phase Shift Image

In some embodiments, in addition to the bright field image generated, a phase shift image results. Phase shift images, which are topographical images of an object, include information about optical distances. In some embodiments, the phase shift image provides information about transparent objects, such as living biological cells, without distorting the bright field image. In some embodiments, digital holographic microscopy allows for both bright field and phase contrast images to be generated without distortion. Also, both visualization and quantification of transparent objects without labeling is possible with digital holographic microscopy. In some embodiments, the phase shift images from digital holographic microscopy can be segmented and analyzed by image analysis software using mathematical morphology, whereas traditional phase contrast or bright field images of living unstained biological cells often cannot be effectively analyzed by image analysis software.

In some embodiments, a hologram includes all of the information pertinent to calculating a complete image stack. In some embodiments, since the object wave front is recorded from a variety of angles, the optical characteristics of the object can be characterized, and tomography images of the object can be rendered. From the complete image stack, a passive autofocus method can be used to select the focal plane, allowing for the rapid scanning and imaging of surfaces without any vertical mechanical movement. Furthermore, a completely focused image of the object can be created by stitching the sub-images together from different focal planes. In some embodiments, a digital reconstruction algorithm corrects any optical aberrations that may appear in traditional microscopy due to image-forming lenses. In some embodiments, digital holographic microscopy advantageously does not require a complex set of lenses; but rather, only inexpensive optics, and semiconductor components are used in order to obtain a well-focused image, making it relatively lower cost than traditional microscopy tools.

Applications

In some embodiments, holographic microscopy can be used to analyze multiple parameters simultaneously in cells, particularly living cells. In some embodiments, holographic microscopy can be used to analyze living cells, (e.g., responses to stimulated morphological changes associated with drug, electrical, or thermal stimulation), to sort cells, and to monitor cell health. In some embodiments, digital holographic microscopy counts cells and measures cell viability directly from cell culture plates without cell labeling. In other embodiments, the imager can be used to examine apoptosis in different cell types, as the refractive index changes associated with the apoptotic process can be quantified via digital holographic microscopy. In some embodiments, digital holographic microscopy is used in research regarding the cell cycle and phase changes. In some embodiments, dry cell mass (which can correlate with the phase shift induced by cells), in addition to other non-limiting measured parameters (e.g., cell volume, and the refractive index), can be used to provide more information about the cell cycle at key points.

In some embodiments, the method is also used to examine the morphology of different cells without labeling or staining. In some embodiments, digital holographic microscopy can be used to examine the cell differentiation process; providing information to distinguish between various types of stem cells due to their differing morphological characteristics. In some embodiments, because digital holographic microscopy does not require labeling, different processes in real time can be examined (e.g., changes in nerve cells due to cellular imbalances). In some embodiments, cell volume and concentration may be quantified, for example, through the use of digital holographic microscopy's absorption and phase shift images. In some embodiments, phase shift images may be used to provide an unstained cell count. In some embodiments, cells in suspension may be counted, monitored, and analyzed using holographic microscopy.

In some embodiments, the time interval between image acquisitions is influenced by the performance of the image recording sensor. In some embodiments, digital holographic microscopy is used in time-lapse analyses of living cells. For example, the analysis of shape variations between cells in suspension can be monitored using digital holographic images to compensate for defocus effects resulting from movement in suspension. In some embodiments, obtaining images directly before and after contact with a surface allows for a clear visual of cell shape. In some embodiments, a cell's thickness before and after an event can be determined through several calculations involving the phase contrast images and the cell's integral refractive index. Phase contrast relies on different parts of the image having different refractive index, causing the light to traverse different areas of the sample with different delays. In some embodiments, such as phase contrast microscopy, the out of phase component of the light effectively darkens and brightens particular areas and increases the contrast of the cell with respect to the background. In some embodiments, cell division and migration are examined through time-lapse images from digital holographic microscopy. In some embodiments, cell death or apoptosis may be examined through still or time-lapse images from digital holographic microscopy.

In some embodiments, digital holographic microscopy can be used for tomography, including but not limited to, the study of subcellular motion, including in living tissues, without labeling.

In some embodiments, digital holographic microscopy does not involve labeling and allows researchers to attain rapid phase shift images, allowing researchers to study the minute and transient properties of cells, especially with respect to cell cycle changes and the effects of pharmacological agents.

Turning to the figures, FIG. 1 depicts one illustrative embodiment of a cell culture incubator (100) having a holographic or phase-contrast imager (102). The cell culture incubator includes an incubator cabinet having an internal chamber (106) for incubation of cells in one or more cell culture vessels. The internal chamber is configured to hold one or more cell culture vessels at a storage location (101). The incubator cabinet includes an external door (105) that opens and closes to permit communication between an external environment and the internal chamber. In some embodiments, the external door (105) opens and closes to permit communication between an external environment and the internal chamber (106).

The incubator cabinet includes a first imaging location (104) where cells can be imaged. The cell culture incubator includes a holographic imager or phase-contrast (102) that images cells of cell culture vessels that are positioned at the first imaging location 104. In one embodiment, the cell culture incubator includes a second imager that images cells at the first imaging location or at another imaging location.

The cell culture incubator includes a transfer device (103) for moving one or more cell culture vessels between the first imaging location (104) and the storage location (101). In some embodiments, the storage location comprises "pigeon holes", or nests, mounted on a circular platform which may rotate to the imaging location (104). In instances where a second imager is present, the transfer device (103) can be used to move the one or more cell culture vessels between the storage location (101) and different imaging locations.

Figure 2:
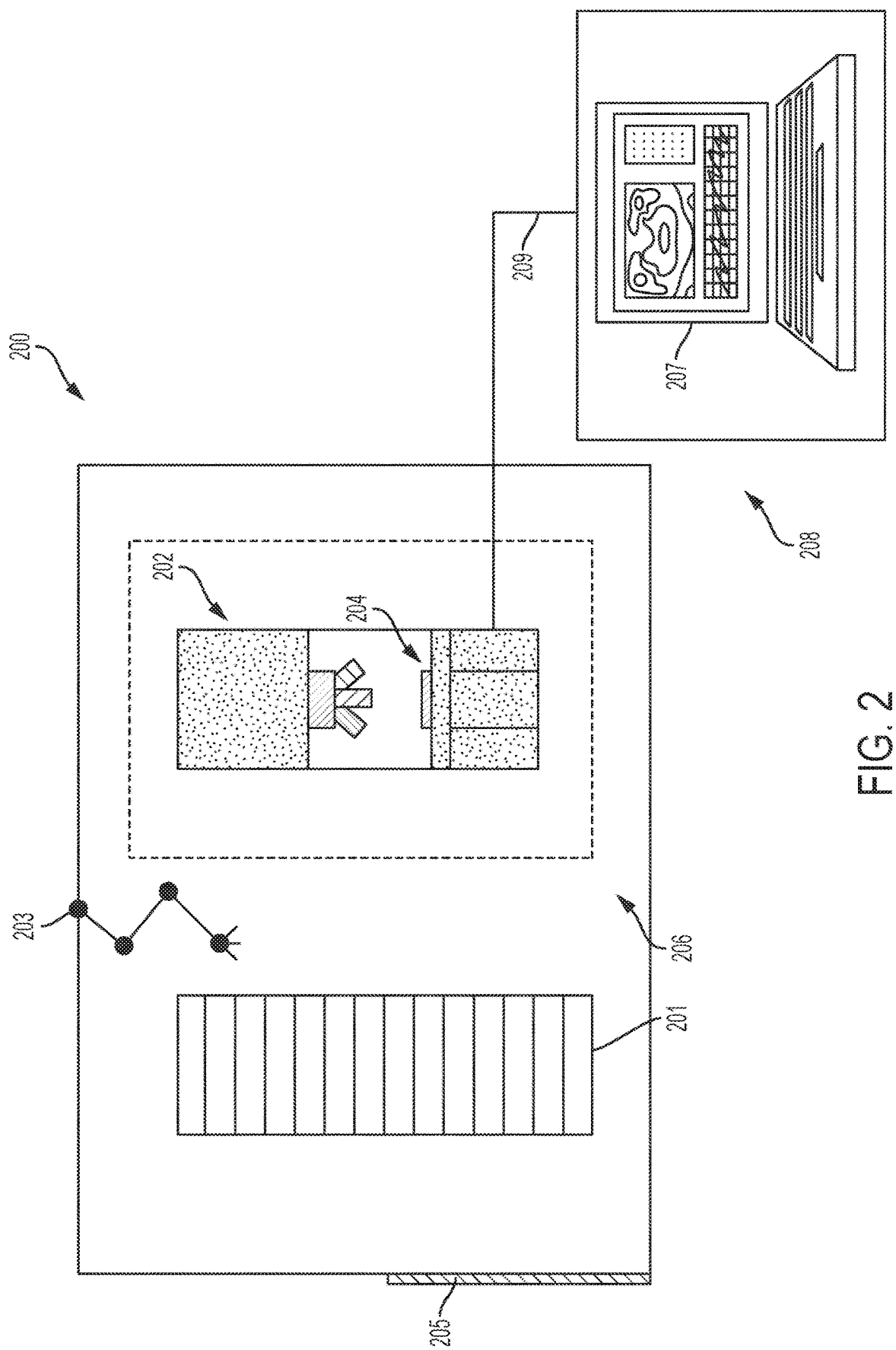
FIG. 2 is a schematic of an automated cell culture incubator having an integrated imaging system, which includes a computer workstation.

FIG. 2 depicts another illustrative embodiment of a cell culture incubator (200) having a holographic or phase-contrast imager (202) and an external computer station (208). As above, the cell culture incubator includes an incubator cabinet having an internal chamber (206) for incubation of cells in one or more cell culture vessels, and the internal chamber (206) is configured to hold one or more cell culture vessels at a storage location (201). The incubator cabinet includes an external door (205) that opens and closes to permit communication between an external environment and the internal chamber. The incubator cabinet includes a first imaging location (204) where cells can be imaged. Cells can be monitored over time (e.g., during a long-term culture) using the holographic or phase-contrast imager (202) by transferring one or more cell culture vessels back and forth between the storage location (201) to the first imaging location (204) using the transfer device (203). The holographic or phase-contrast imager (202) can be used to acquire images of the cells. Image information from the holographic or phase-contrast imager (202) can be transferred to the external computer station (208) via a communication line (209).

A computer (207) is provided with a display to permit a user to monitor cultures externally, e.g., by visualizing images on a display. In some cases, images can be stored, processed and analyzed automatically using image processing and analytical techniques implemented by the computer (207) to produce quantitative information regarding cell growth, development, viability, health, differentiation state, or other parameters. This quantitative information can be used to assess long term cultures and ensure cell health or other desired conditions. This information, along with the images, can be stored in a manner that permits correlation with other acquired data such as timestamps and sensor outputs. Storage can be in a database or in a file system.

Storage can consist of selected images or a complete history of every image captured. While a communication line (209) is depicted in this illustrative embodiment for sending image information between the holographic or phase-contrast imager (202) and the computer (207), a hard communication line need not be used in all cases. For example, in some embodiments, information can be communicated between the holographic or phase-contrast imager (202) and a computer (207) wirelessly (e.g., using Bluetooth technology, WIFI, or other means of wireless communication). Similarly, a computer at which images from the holographic or phase-contrast imager (202) are analyzed or viewed need not be in close proximity to the incubator. For example, a computer can be in another room, another building, or at a remote location. In such cases information can be passed between the holographic or phase-contrast imager (202) and computer (207) through a wireless network, a local network, over the Internet, or other appropriate means.

Figure 3:
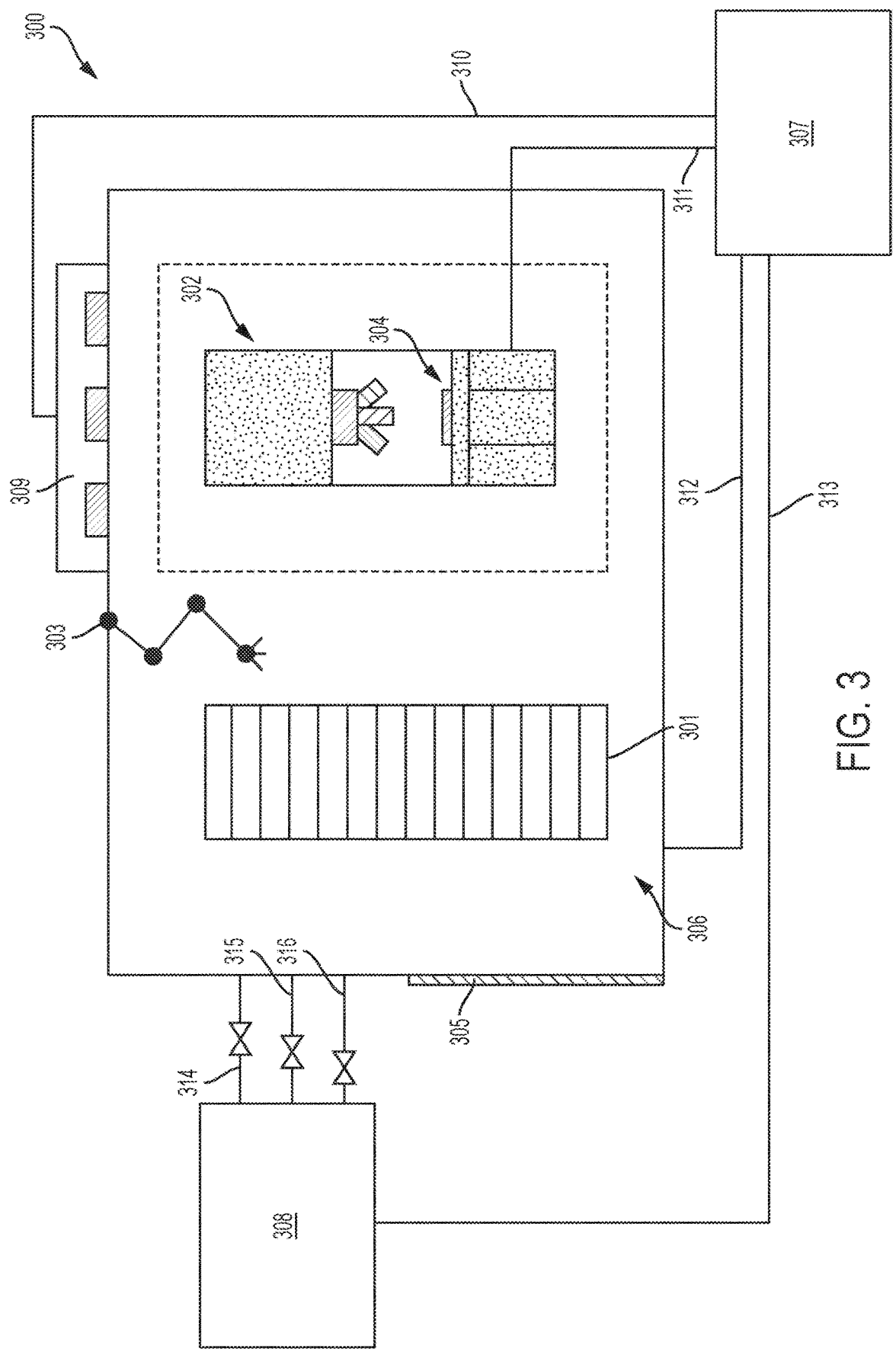
FIG. 3 is a schematic of an automated cell culture incubator having an integrated imaging system and an environmental control system.

FIG. 3 depicts another illustrative embodiment of a cell culture incubator (300) having a holographic or phase-contrast imager (302), a control and monitoring station (307) and an environmental control station (308). As above, the cell culture incubator includes an incubator cabinet having an internal chamber (306) for incubation of cells in one or more cell culture vessels, and the internal chamber is configured to hold one or more cell culture vessels at a storage location (301). The incubator cabinet includes an external door (305) that opens and closes to permit communication between an external environment and the internal chamber. The incubator cabinet includes a first imaging location (304) where cells can be imaged. Here again, cells can be monitored over time (e.g., during a long-term culture) using the holographic or phase-contrast imager (302) by transferring one or more cell culture vessels back and forth between the storage location (301) to the first imaging location (304) using the transfer device (303). The holographic or phase-contrast imager (302) can be used to acquire images of the cells. Image information from the holographic or phase-contrast imager (302) can be transferred to the external control and monitoring station (307) via a communication line (311).

A sensor panel (309) is provided which includes one or more sensors for measuring environmental conditions relevant to maintenance of cell growth, which may include temperature, $CO_2$, $O_2$, humidity or other relevant parameters. A sensor communication line (310) is provided to transfer information between the sensors and the control and monitoring station (307). The control and monitoring station includes a controller that may produce one or more control outputs to the environmental control station (308) in response to input from the sensor panel 309. For example, if the controller receives a signal from the sensor panel that one or more environmental parameters is outside a desired set point, the controller can send an appropriate signal to the environmental control station (308), in response to which the environment control station (308) can control operation of an appropriate fluid supply line (314-316) to introduce an appropriate gas or fluid or other medium into the internal chamber to restore the environmental conditions to a desired state.

In a more specific example, the controller may receive a signal from the sensor panel that $CO_2$ levels are below a desired set point (e.g., below 5% $CO_2$. In response to the signal, the controller can send an appropriate signal to the environmental control station (308), in response to which the environment control station (308) can control operation of a $CO_2$ supply line (314). The $CO_2$ supply line (314) can introduce $CO_2$ into the internal chamber to restore the $CO_2$ to the desired set point. In another example, the controller may receive a signal from the sensor panel that humidity levels are below a desired set point (e.g., below 80% humidity). In response to the signal, the controller can send an appropriate signal to the environmental control station (308), in response to which the environment control station (308) can control operation of a water vapor supply line (315). The water vapor supply line can introduce water vapor into the internal chamber to restore the humidity to the desired set point. In another example, the controller may receive a signal from the sensor panel that incubator temperature is above or below a desired set point (e.g., above or below 37° C.). In response to the signal, the controller can send an appropriate signal to incubator jacket heater via heater control line (312), in response to which the incubator jacket heater can be appropriately modulated to increase or decrease the temperature in the incubator to restore the temperature to the desired set point.

In some embodiments, the holographic or phase-contrast imager (302) can be used to acquire images of cells. Image information from the holographic or phase-contrast imager (302) can be transferred to the control and monitoring station (307) via a communication line (311). The control and monitoring station (307) can be fitted with a computer configured to process image information and produce appropriate control signals based on the processed image information. In this way, environmental conditions inside the chamber can be adjusted and controlled not only based on information from environmental sensors (e.g., $CO_2$, humidity, or temperature sensors) but also from, or alternatively from, information regarding cell growth or health obtained from imaging cells within the automated incubator that is indicative of a need to alter the environmental conditions. For example, cells may exhibit characteristic changes that can be detected by imaging when the pH of a surrounding medium drops below a physiologically appropriate level which may indicate that $CO_2$ levels in the chamber need to be adjusted. The characteristic changes can be detected by imaging, and the environmental control station (308) can operate to restore the conditions.

Cell Culture Vessels

Aspects of the disclosure relate to incubators and methods for culturing, manipulating, and/or monitoring cells under controlled conditions (e.g., under aseptic and/or sterile conditions). In some embodiments, cell cultures are grown within a culture vessel in an incubator of the disclosure. As used herein, a "cell culture vessel" is a device including a housing and one or more chambers for culturing cells. In some embodiments, the housing is a frame. The frame may be coupled to a lid. The one or more chambers may include cell culturing media including one or more membranes. In some embodiments, a cell culture vessel may include nutrients for promoting the growth of cells. In certain embodiments, a cell culture vessel may entirely enclose one or more cells or groups thereof. The housing of a cell culture vessel may include one or more pores or openings to permit the transfer of gases between a cell culture vessel and its surrounding environment. In certain embodiments, a cell culture vessel includes a transparent or optically clear window. For example, a lid coupled to the housing of a cell culture vessel may include an optically clear portion for viewing cells e.g., with a microscope or other imager. In some embodiments, a cell culture vessel includes one or more portions that are substantially non-reflective.

Cell culture vessels may be configured for culturing cells of different types, including eukaryotic or prokaryotic cells.

In some embodiments, cells are mammalian cells (e.g., human cells, canine cells, bovine cells, ovine cells, feline cells, or rodent cells such as rabbit, mouse, or rat cells). In some embodiments, cells are insect cells, avian cells, microbial cells (e.g., yeast cells such as *Saccharomyces cerevisiae, Kluyveromyces lactis*, or *Pischia pastoris* cells, or bacterial cells such as *Escherichia coli, Bacillus subtilis*, or *Corynebacterium* cells), insect cells (e.g., *Drosophila* cells, or Sf9 or Sf21 cells), plant cells (e.g., algal cells) or cells of any other type.

In some embodiments, cell culture vessels may be pre-kitted with one or more reagents desired for a particular purpose, e.g., for growing cells, for differentiating cells, for subjecting cells to a particular assay condition, etc. In some embodiments, pre-kitted cell culture vessels contain reagents useful for performing a particular experiment (e.g., cell growth media, growth factors, selection agents, labeling agents, etc.) on a cell culture, in advance of the experiment. Pre-kitted cell culture vessels may facilitate experimental protocols by providing cell culture-ready vessels that do not require the addition of reagents. For example, progenitor cells from a patient may be added to a cell culture vessel pre-kitted with reagents for cell differentiation for the purpose of expanding a population of differentiated cells for autologous cell therapy. Pre-kitted cell culture vessels can be stored at any appropriate temperature, which is determined by the recommended storage parameters of the reagents within the pre-kitted cell culture vessel. In some embodiments, pre-kitted cell culture storage vessels are stored prior to use at temperatures between about −80° C. and about 37° C. In some embodiments, pre-kitted cell culture storage vessels are stored prior to use at temperatures between about −80° C. and about −20° C. In some embodiments, pre-kitted cell culture storage vessels are stored prior to use at temperatures between about −20° C. and about 4° C. In some embodiments, pre-kitted cell culture storage vessels are stored prior to use at temperatures between about 4° C. and about 37° C. In some embodiments, pre-kitted cell culture vessels are disposable. In some embodiments, pre-kitted cell culture vessels are reusable and/or refillable.

In some embodiments, cells are cultured for producing natural products (e.g., taxols, pigments, fatty acids, biofuels, etc.). In some embodiments, cells are cultured to express recombinant products (e.g., recombinant protein products such as antibodies, hormones, growth factors, or other therapeutic peptides or proteins). In some embodiments, cells are expanded and/or differentiated for therapeutic use such as implantation into a subject (e.g., a human subject) in order to provide or supplement a cellular, tissue, or organ function that is missing or defective in the subject.

In some embodiments, cells are from immortalized cell lines. Non-limiting examples of cell lines include human cells, for example HeLa cells, prostate cancer cells (e.g., DU145, PC3 and/or Lncap cells), breast cancer cells (e.g., MCF-7, MDA-MB-438, and/or T47D cells), acute myeloid leukemia cells (e.g., THP-1 cells), glioblastoma cells (e.g., U87 cells), neuroblastoma cells (e.g., SHSY5Y cells), bone cancer cells (e.g., Saos-2 cells) and chronic myelogenous leukemia cells (e.g., KBM-7 cells). In some embodiments, cell lines include primate cell lines, rodent cell lines (e.g., rat or mouse cell lines), canine cell lines, feline cell lines, Zebrafish cell lines, Xenopus cell lines, plant cell lines, or any other cell lines. In some embodiments, cells are human 293 cells (e.g., 293-T or HEK 293 cells), murine 3T3 cells, Chinese hamster ovary (CHO) cells, CML T1 cells, or Jurkat cells.

In some embodiments, cells are primary cells, feeder cells, or stem cells. In some embodiments, cells are isolated from a subject (e.g., a human subject). In some embodiments, cells are primary cells isolated from a tissue or a biopsy sample. In some embodiments, cells are hematopoietic cells. In some embodiments, cells are stem cells, e.g., embryonic stem cells, mesenchymal stem cells, cancer stem cells, etc. In some embodiments, cells are isolated from a tissue or organ (e.g., a human tissue or organ), including but not limited to solid tissues and organs. In some embodiments, cells can be isolated from placenta, umbilical cord, bone marrow, liver, blood, including cord blood, or any other suitable tissue. In some embodiments, patient-specific cells are isolated from a patient for culture (e.g., for cell expansion and optionally differentiation) and subsequent re-implantation into the same patient or into a different patient. Accordingly, in some embodiments, cells grown in the incubators disclosed herein may be used for allogenic or autogeneic therapy. In some embodiments, cells grown in the incubators disclosed herein may be genetically modified, expanded and reintroduced into a patient for the purpose of providing an immunotherapy (e.g., chimeric antigen receptor therapy (CAR-T), or delivery of CRISPR/Cas modified cells).

In some embodiments, a primary cell culture includes epithelial cells (e.g., corneal epithelial cells, mammary epithelial cells, etc.), fibroblasts, myoblasts (e.g., human skeletal myoblasts), keratinocytes, endothelial cells (e.g., microvascular endothelial cells), neural cells, smooth muscle cells, hematopoietic cells, placental cells, or a combination of two or more thereof.

In some embodiments, cells are recombinant cells (e.g., hybridoma cells or cells that express one or more recombinant products). In some embodiments, cells are infected with one or more viruses.

Primary Cell Isolation

In some embodiments, cells are isolated from tissues or biological samples for ex vivo culture in the incubators provided herein. In some embodiments, cells (e.g., white blood cells) are isolated from blood. In some embodiments, cells are released from tissues or biological samples using physical and/or enzymatic disruption. In some embodiments, one or more enzymes such as collagenase, trypsin, or proteinase are used to digest the extracellular matrix. In some embodiments, tissue or biological samples are placed in culture medium (e.g., with or without physical or enzymatic disruption) and cells that are released and that grow in the culture medium can be isolated for further culture.

Cell Culture

As used herein, cell culture refers to a procedure for maintaining and/or growing cells under controlled conditions (e.g., ex vivo). In some embodiments, cells are cultured under conditions to promote cell growth and replication, conditions to promote expression of a recombinant product, conditions to promote differentiation (e.g., into one or more tissue specific cell types), or a combination of two or more thereof.

In some embodiments, cell culture vessels are configured for culturing cells in suspension. In some embodiments, cell culture vessels are configured for culturing adherent cells. In some embodiments, cell culture vessels are configured for 2D or 3D cell culture. In some embodiments, cell culture vessels include one or more surfaces or micro-carriers to support cell growth. In some embodiments, these are coated with extracellular matrix components (e.g., collagen, fibrin and/or laminin components) to increase adhesion properties and provide other signals needed for growth and differentiation. In some embodiments, cell culture vessels include one or more synthetic hydrogels such as polyacrylamide or polyethylene glycol (PEG) gels to support cell growth. In some embodiments, cell culture vessels include a solid support with embedded nutrients (e.g., a gel or agar, for example, for certain bacterial or yeast cultures). In some embodiments, cell culture vessels include a liquid culture medium.

In some embodiments, cells are cultured in one of any suitable culture media. Different culture media having different ranges of pH, glucose concentration, growth factors, and other supplements can be used for different cell types or for different applications. In some embodiments, custom cell culture media or commercially available cell culture media such as Dulbecco's Modified Eagle Medium, Minimum Essential Medium, RPMI medium, HA or HAT medium, or other media available from Life Technologies or other commercial sources can be used. In some embodiments, cell culture media include serum (e.g., fetal bovine serum, bovine calf serum, equine serum, porcine serum, or other serum). In some embodiments, cell culture media are serum-free. In some embodiments, cell culture media include human platelet lysate (hPL). In some embodiments, cell culture media include one or more antibiotics (e.g., actinomycin D, ampicillin, carbenicillin, cefotaxime, fosmidomycin, gentamycin, kanamycin, neomycin, penicillin, penicillin streptomycin, polymyxin B, streptomycin, tetracycline, or any other suitable antibiotic or any combination of two or more thereof. In some embodiments, cell culture media include one or more salts (e.g., balanced salts, calcium chloride, sodium chloride, potassium chloride, magnesium chloride, etc.). In some embodiments, cell culture media include sodium bicarbonate. In some embodiments, cell culture media include one or more buffers (e.g., HEPES or other suitable buffer). In some embodiments, one or more supplements are included. Non-limiting examples of supplements include reducing agents (e.g., 2-mercaptoethanol), amino acids, cholesterol supplements, vitamins, transferrin, surfactants (e.g., non-ionic surfactants), CHO supplements, primary cell supplements, yeast solutions, or any combination of two or more thereof. In some embodiments, one or more growth or differentiation factors are added to cell culture media. Growth or differentiation factors (e.g., WNT-family proteins, BMP-family proteins, IGF-family proteins, etc.) can be added individually or in combination, e.g., as a differentiation cocktail comprising different factors that bring about differentiation toward a particular lineage. Growth or differentiation factors and other aspects of a liquid media can be added using automated liquid handlers integrated as part of an incubator provided herein.

In some aspects, the incubators and methods described herein provide and maintain appropriate temperature and gas mixtures for cell growth. It should be appreciated that cell growth conditions differ for different cell types and that the incubators described herein can be programmed to maintain different conditions. In some embodiments, conditions of approximately 37° C., and 5% $CO_2$ are used for mammalian cells.

In some embodiments, devices and methods described herein are used to monitor or assay the culture media for nutrient depletion, changes in pH, changes in temperature accumulation of apoptotic or necrotic cells, and/or cell density. In some embodiments, devices and methods described herein are used to modify or change the culture media or conditions and/or to passage the cell cultures when appropriate. In some embodiments, these procedures are automated.

In some embodiments (e.g., for adherent cell cultures), culture media can be removed directly by aspiration and replaced with fresh media. In some embodiments (e.g., for non-adherent/suspension cultures), media changes can involve centrifuging a cell culture, removing the old culture media and replacing it with fresh media. In some embodiments, the centrifuge is located in the internal chamber of an incubator. In some embodiments, culture vessels allow for continuous media replacement. In some embodiments, the incubators described herein may include one or more components that can be used to process, replace, supply, and/or maintain different aspects of a culture media to support cells. Incubators may include a reservoir containing waste media and/or a reservoir containing fresh media. Such reservoirs may be present (e.g., for temporary storage) within a refrigerator inside the incubator or a refrigerated section of the incubator. In some embodiments, one or more reservoirs are provided outside the incubators and piping is provided into and out from the incubator space to supply or draw from a liquid handler units (e.g., liquid handle units having an aspirator) or temporary reservoir within the incubator to facilitate cells feeding, media changes, and other related needs. For suspension cells, devices may be provided within the incubator to separate cells from waste media (e.g., centrifuge(s) to facilitate cell pelleting) to facilitate automated media changes as part of an incubator provided herein. In some embodiments, the document provides a system comprising a cell culture incubator connected to a computer, capable of automatically monitoring and adjusting cell culture conditions for optimal growth of the cell culture.

In some embodiments, cells are passaged within an incubator cabinet described herein. In some embodiments, a cell culture is split and a subset of the cell culture is transferred to a fresh culture vessel for further growth. In some embodiments (e.g., for adherent cell cultures), cells are detached (e.g., mechanically, for example using gentle scraping, and/or enzymatically, for example using trypsin-EDTA or one or more other enzymes) from a surface prior to being transferred to a fresh culture vessel. In some embodiments (e.g., for suspension cell cultures), a small volume of a cell culture is transferred to a fresh culture vessel.

In some embodiments, cell cultures are manipulated in other ways during culture within an incubator cabinet of an incubator herein. For example, cell cultures may be transfected with nucleic acids (e.g., DNA or RNA) or exposed to viral infection (e.g., using recombinant virus particles to deliver DNA or RNA), while for example, remaining within an incubator cabinet of an incubator provided herein.

It should be appreciated that aseptic techniques can be used to prevent or minimize contamination of cell cultures during growth and manipulation. In some embodiments equipment (e.g., pipettes, fluid handling devices, manipulating devices, other automated or robotic devices, etc.) that is used for cell culture is sterilized using an appropriate technique. Non-limiting techniques include heat exposure (e.g., autoclaving) surface disinfection (e.g., using alcohol, bleach, or other disinfectant), irradiation, and/or exposure to a disinfectant gas (e.g., ozone, hydrogen peroxide, etc.) as described herein. In some embodiments, media is sterilized using an appropriate technique. Non-limiting techniques include heat exposure (e.g., autoclaving), antimicrobial/antiviral treatment, filtration, and/or irradiation.

In some embodiments, manipulations of cell cultures are performed under aseptic conditions, for example, in an environment (e.g., within an incubator chamber) that has been disinfected and in which the air has been filtered to remove potential contaminants.

In some embodiments, cell cultures are grown and maintained under GMP-compliant conditions, including those that include using GMP-compliant media or GMP-compliant liquid handling equipment. In some cases, cell cultures are grown and maintained by performing methods in conjunction with standard operation procedures (SOPs).

In some embodiments, cell cultures can be monitored and/or evaluated to detect contamination. In some embodiments, contamination by cells from a different type of organism can be detected. In some embodiments, contamination of a mammalian cell culture by mycoplasma, bacteria, yeast, or viruses can be detected using any suitable technique. In some embodiments, cell culture contamination can be detected by assaying for changes or for rates of change of one or more culture properties such as pH, turbidity, etc., that are characteristic of contamination (e.g., by bacteria or yeast) and not characteristic of the cells (e.g., mammalian cells) being grown in culture. In some embodiments, one or more molecular detection assays (e.g., PCR, ELISA, RNA labeling or other enzymatic techniques) or cell-based assays can be used to detect contamination (e.g., mycoplasma, bacterial, yeast, viral, or other contamination).

In some embodiments, cell cultures can be monitored and/or evaluated to detect contamination with cells of similar types (e.g., a human cell line contaminated by different human cells or by different mammalian cells). In some embodiments, cell cultures and their potential contamination can be evaluated using DNA sequencing or DNA fingerprinting (e.g., short tandem repeat-STR-fingerprinting), isoenzyme analysis, human lymphocyte antigen (HLA) typing, chromosomal analysis, karyotyping, cell morphology, or other techniques.

In some embodiments, cells produced using the incubators or methods described herein can be frozen to preserve them for later use and/or for transport. In some embodiments, cells are mixed with a cryopreservation composition after growth and/or differentiation and prior to freezing. A cryopreservation composition can be added to a cell culture vessel or cells can be transferred from a cell culture vessel to a cryopreservation vessel along with a cryopreservation composition. Non-limiting examples of cryoprotectants that can be included in a cryopreservation composition include DMSO, glycerol, PEG, sucrose, trehalose, and dextrose. In some embodiments, a freezer may be provided as a component of an incubator to facilitate freezing of cells isolated from cell cultures. For example, one or more freezers may be located in an internal chamber and/or integrated into the incubator cabinet (e.g., into the wall of the incubator cabinet).

Cell Culture Incubators

In some embodiments this document relates to incubators and methods for culturing, manipulating, and/or monitoring cells under controlled conditions (e.g., under aseptic and/or sterile conditions). In some embodiments, the cell culture incubators included an incubator cabinet having an internal chamber for incubation of cells in one or more cell culture vessels. In some cases, in addition to an internal door from the transfer chamber to the internal chamber, the incubators include at least one external door (e.g., 1, 2, 3, 4, or more external doors) opening from an external environment directly to the internal chamber, for example, to provide alternative access to the internal chamber during periods of time when the incubator is not operational, e.g., during maintenance of the incubator. In some embodiments, incubators include a storage location within the internal chamber for storing one or more cell culture vessels.

As used herein, an "incubator cabinet" is a housing that includes one or more chambers configured to hold one or more cell culture vessels. In some embodiments, an incubator cabinet includes a transfer chamber and an internal chamber, one or both of which are configured to hold one or more cell culture vessels. In some embodiments, an incubator may include one or more other elements such as one or more gas sources (e.g., a gas cylinder or ozone generator), tubing (e.g., to convey one or more liquids or gases such as water, distilled water, deionized water, cell culture medium, air, carbon dioxide, ozone, and oxygen), airflow mechanisms (e.g., valves, release valves, pinholes, gas regulators, and mass flow regulators), pressure mechanisms (e.g., a pump such as a dry scroll pump, rotary pump, momentum transfer pump, diffusion pump, or diaphragm pump; a suction tube; a vacuum system; and an air blower), environmental monitors and controls (e.g., a gas sensor and/or monitor to sense and/or control concentrations of gases such as carbon dioxide, oxygen, and ozone; heat sources or sinks; temperature monitors and controls; humidity monitors; gas scrubbers; air filters; instrumentation for measuring particulate matter; pressure gauges; and flow meters), doors (e.g., openings or panels) windows (e.g., optical windows made of glass, plastic, composite, or other substantially transparent material for viewing an area inside the incubator), ports (e.g., to permit the introduction or removal of one or more gases or liquids), light sources (e.g., lamps, bulbs, lasers, and diodes), optical elements (e.g., microscope objectives, mirrors, lenses, filters, apertures, wave plates, windows, polarizers, fibers, beam splitters, and beam combiners), imaging elements (e.g., cameras, barcode readers), electrical elements (e.g., circuits, cables, power cords, and power supplies such as batteries, generators, and direct or alternating current supplies), computers, mechanical elements (e.g., motors, wheels, gears, robotic elements, and actuators such as pneumatic actuators, electromagnetic actuators, motors with cams, piezoelectric actuators, and motors with lead screws), and control elements (e.g., spin-wheels, buttons, keys, toggles, switches, cursors, screws, dials, screens, and touch-screens). In some embodiments, one or more of these other elements are part of the incubator, but are external to the incubator cabinet. In some embodiments, one or more of these other elements are included within the incubator cabinet.

In some embodiments, incubators or incubator cabinets provided herein are rectangularly cuboidal in shape. In some embodiments incubators or incubator cabinets provided herein have a rectangular footprint in a range of 1 $ft^2$ to 16 $ft^2$. In some embodiments incubators or incubator cabinets provided herein have a rectangular footprint of up to about 1 $ft^2$, 2 $ft^2$, 3 $ft^2$, 4 $ft^2$, 5 $ft^2$, 6 $ft^2$, 7 $ft^2$, 8 $ft^2$, 9 $ft^2$, 10 $ft^2$, 11 $ft^2$, 12 $ft^2$, 13 $ft^2$, 14 $ft^2$, 15 $ft^2$, or 16 $ft^2$. In some embodiments incubators or incubator cabinets provided herein have a total chamber volume in a range of 1 $ft^3$ to 100 $ft^3$. In some embodiments incubators or incubator cabinets provided herein have a chamber volume of up to about 1 $ft^3$, 5 $ft^3$, 10 $ft^3$, 25 $ft^3$, 50 $ft^3$ or 100 $ft^3$. In some embodiments incubators or incubator cabinets provided herein have a rectangular footprint in a range of 0.09 $m^2$ to 1.78 $m^2$. In some embodiments incubators or incubator cabinets provided herein have a rectangular footprint of up to about 0.1 $m^2$, 0.2 $m^2$, 0.3 $m^2$, 0.4 $m^2$, 0.5 $m^2$, 0.6 $m^2$, 0.7 $m^2$, 0.8 $m^2$, 0.9 $m^2$, 1.0 $m^2$, 1.1 $m^2$, 1.2 $m^2$, 1.3 $m^2$, 1.4 $m^2$, 1.5 $m^2$, 1.6 $m^2$, or 1.7 $m^2$. In some embodiments, incubators or incubator cabinets provided herein have a total chamber volume in a range of 0.03 m³ to 3 m³. In some embodiments incubators or incubator cabinets provided herein have a chamber volume of up to about 0.03 m³, 0.1 m³, 0.3 m³, 1 m³, or 3 m³.

Storage Locations

As used herein, a "storage location" refers to a location at which one or more cell culture vessels is stored (e.g. within an incubator cabinet). For example, one or more cell culture vessels may be stored at a storage location and later transferred to a different location (e.g., an imaging location). The storage location may be disposed in the internal chamber of the incubator cabinet. A storage location may be configured for storing a plurality of cell culture vessels. For example, a storage location may include one or more storage arrays, racks, shelves, pigeon-holes, cubbies, trays, slots, or other positions or mechanisms. In some embodiments, a storage location may be configured to store cell culture vessels horizontally, while in other embodiments it may be configured to store cell culture vessels vertically. For example, a storage location may include a plurality of slots to receive cell culture vessels stacked vertically over one another. A storage location may be configured to hold 1, 2, 3, 4, 5, 6, 7, 8, 9, 10, 15, 20, 25, 30, 35, 40, 45, 50, 100, or any other number of cell culture vessels. In some embodiments, a storage location may be configured to hold greater than 100 cell culture vessels. In some embodiments, a storage location may include a mechanism for moving one or more storage arrays, racks, shelves, pigeon-holes, cubbies, trays, slots, or other positions or mechanisms. For example, a storage location may include one or more motors and movable stages (e.g., an xy or xyz stage) to move a storage rack from one position in an internal chamber to another position in an internal chamber, e.g., to facilitate access to one or more cell culture vessels stored in different locations. In some embodiments, the incubator cabinet may include one or more cell culture vessel transfer devices for moving one or more cell culture vessels.

A storage location may be configured to securely hold or receive one or more cell culture vessels. For example, one or more components of the storage location may include one or more locking mechanisms that have one or more adhesive, magnetic, electrical, and/or mechanical components (e.g., snaps, fasteners, locks, clasps, gaskets, o-rings, septa, springs, and other engagement members). In some embodiments, a storage location and/or cell culture vessel may include one or more grooves or depressions and/or may involve pieces of molded plastic. For example, a cell culture vessel may include one or more protruded features (e.g., a rim or knob) that is molded for insertion into one or more corresponding grooves, holes, or depressions at a storage location. In some cases, a cell culture vessel may include one or more grooves, holes, or depressions that are molded to fit one or more corresponding protruded features at a storage location.

As used herein, a "fiducial mark" refers to a feature that facilitates alignment of one or more components. In some embodiments, fiducial marks may include one or more hole apertures over a fluorescent media or printed or embossed fluorescent material. In other embodiments, fiducial marks may include grids, lines, or symbols. In some embodiments, one or more cell culture vessels include one or more fiducial marks to facilitate alignment of one or more cell culture vessels with an imager.

Materials

In some embodiments, an incubator cabinet is single-walled. In some embodiments, an incubator is double-walled. In some embodiments, insulation material is provided between the double walls of an incubator cabinet to control heat loss from the incubator cabinet and facilitate temperature control in the incubator cabinet. In some embodiments, the outer wall of an incubator cabinet comprises a sheet metal, e.g., a 14-20 gauge cold rolled steel. In some embodiments, an inner wall (e.g., a chamber surface) of an incubator cabinet includes electro-polished stainless steel. In some embodiments, an inner wall (e.g., a chamber surface) of an incubator cabinet includes corrosion resistant materials, such as, titanium, cobalt-chrome, tantalum, platinum, zirconium, niobium, stainless steel, and alloys thereof. However, in some embodiments, a chamber surface of an incubator cabinet includes a polymeric material such as polytetrafluoroethylene (PTFE), or a polymeric material know under the trade name of Parylene. In some embodiments, a chamber surface may have anti-microbial properties, such as copper or silver or anti-microbial compounds incorporated into a polymeric surface coating.

Monitoring Equipment

In some embodiments, the environment inside an incubator is controlled by a control system that may be configured to control the temperature, humidity, carbon dioxide, oxygen and other gaseous components (e.g., sterilization gases, such as, ozone, and hydrogen peroxide) inside the incubator (e.g., in one or more internal chambers). In some embodiments, a control system controls the environmental conditions (e.g., temperature, humidity, carbon dioxide, oxygen and other gaseous components) within each internal chamber separately. For example, in order to protect sensitive mechanical, electronic and optical components, the humidity of an internal chamber may be maintained at a lower level than an internal chamber having a storage location. In some embodiments, the incubator is further provided with a monitoring system with predefined sensors. Examples of monitoring devices include but are not limited to oxygen monitors, carbon dioxide monitors, ozone gas detectors, hydrogen peroxide monitors and multi gas monitors. For example, in some embodiments, an incubator advantageously includes a plurality of sensors responsive to different parameters relevant to cell growth, which may include temperature, air purity, contaminant levels, pH, humidity, $N_2$, $CO_2$, $O_2$ and light. By means of this monitoring system, parameters in the incubator can be measured using sensors for the duration of a culture or process. In some embodiments, parameters measured by the sensors are transmitted by the monitoring system via a line to a computer-controlled monitoring and control system for further processing as discussed elsewhere herein.

In some embodiments, an environmental monitoring system can be used in conjunction with an incubator described herein. In some embodiments, one or more sensors that provide for the measurement of temperature, air composition (e.g., $CO_2$ concentration, $O_2$ concentration, etc.), and/or humidity of the system can be associated with an incubator (e.g., fitted within an incubator cabinet). In some embodiments, one or more such sensors can be incorporated as part of an incubator (e.g., attached to, integral to, or otherwise connected to an internal wall or door of the incubator). In some cases, one or more sensors can be positioned at any suitable location(s) outside or inside an incubator cabinet (e.g., within a transfer chamber and/or an internal chamber, for example attached to an internal wall, and/or upper or lower internal surface).

In some embodiments, a gas sensor is provided that can provide a reading in real time of the concentration of gas in contact with the sensor (e.g., gas in a cabinet, or ambient air) in percent, parts per million, or any other standard unit. Gas sensors for use in the methods and incubators provided herein include $CO_2$ sensors, $O_2$ sensors, $N_2$ sensors, ozone gas detectors, hydrogen peroxide monitors, multi gas monitors, and CO sensors. Such sensors are available from a number of commercial sources. In some cases, the environment of the incubator may be modulated or controlled based upon the information provided by the sensors described herein. For example, the level of $CO_2$ in an incubator may be increased upon indication from a $CO_2$ sensor that a lower than desirable concentration of $CO_2$ is present in the incubator.

In some embodiments, one or more heating or cooling elements can be incorporated within the incubator (e.g., on an inner surface of the cabinet or door, and/or integrated within one or more of the walls and/or the base of the cabinet) for purposes of controlling the temperature within the incubator. In some embodiments, a heating element can be used for thawing liquids, for example, cell culture media or other reagents. In some embodiments, one or more air or oxygen sources, carbon filters, and/or one or more humidification or dehumidification systems are connected to the incubator and configured to control the level of oxygen, carbon dioxide, and/or humidity within the incubator (e.g., in response to signals from the one or more sensors in or attached to the incubator).

In some embodiments, an incubator can include one or more light sources (e.g., an incandescent bulb, LED, UV or other light source). These can be placed within the incubator to illuminate regions within the cabinet. In some embodiments, the culture system operation is monitored using a camera or other light sensitive device that can be placed within or outside the incubator. In some embodiments, the light source is a sterilizing light source. For example, a UV lamp may be located within the transfer chamber and/or the interior chamber of the incubator provided herein.

In some embodiments, the incubator includes a transparent object (e.g., window) that allows visible light or other light wavelengths from within the incubator to be detected by a camera or other light sensitive device placed outside the incubator. In some embodiments, the inner surface of the transparent object can be wiped (e.g., from the inside of the cabinet) to prevent or remove condensation droplets that may accumulate (e.g., due to the humid air inside the incubator) on the inner surface and interfere with the monitoring of the system. In some embodiments, the surface can be wiped by a wiper that is automatically controlled by a controller.

Doors

As used herein, a "door" is an element that permits communication between two or more environments or regions when opened and prevents communication between the two or more environments or regions when closed. A door may be of any type, such as a sliding door, pocket door, swinging door, hinged door, revolving door, pivot door, or folding door. The door may be manually, mechanically, or electrically operated. For example, an operator may open or close a door by manually grasping, pulling, pushing, and/or otherwise physically interacting with the door or an element thereof (e.g., a handle) or by operating a mechanical control (e.g., a button, toggle, spin-wheel, key, switch, cursor, screw, dial, screen, or touch-screen). In certain embodiments, a door may be controlled by electrical or digital controls, such as by a computer. A door may be an automatically opening door. For example, a door may include a sensor, such as a pressure, infrared, motion, or remote sensor, that detects whether the door is open or closed and/or controls when the door opens or closes. A door may open by mechanical, pneumatic, electrical, or other means. In some embodiments, one or more doors may include one or more locking mechanisms. In particular environments, one or more doors may include one or more interlocks (e.g., a mechanical interlock such as a pin, bar, or lock or an electrical interlock such as a switch) to prevent one or more doors from opening at an undesirable time (e.g., when one or more chambers are open to the outside environment).

Seals

In some embodiments, an incubator (e.g., an internal chamber, and/or a transfer chamber of an incubator cabinet) comprises one or more windows and/or doors, that, when closed, are sealed to preserve sterility (e.g., after one or more chambers of the incubator have been sterilized). In some embodiments, each seal of the incubator is air tight up to a threshold level of pressure (e.g., up to 1 atm). In some embodiments, a gasket is provided to ensure a desired level of sealing capacity. In general, a "gasket" is understood as a mechanical seal that fills the space between two objects, generally to prevent leakage between the two objects while under compression. Gaskets are commonly produced by cutting from sheet materials, such as gasket paper, rubber, silicone, metal, cork, felt, neoprene, nitrile rubber, fiberglass, or a plastic polymer (such as polychlorotrifluoroethylene). It is often desirable that a gasket be made from a material that provides some degree of yielding such that it is able to deform and fill tightly the space it is designed for, including any slight irregularities. In some embodiments, gaskets can be used with an application of sealant directly to the gasket surface to function properly. In some embodiments, a gasket material can be a closed-cell neoprene foam which is non-reactant with carbon dioxide or ozone.

Transfer Devices

As used herein, a "transfer device for moving one or more items" refers to a device that can transfer one or more items from a first location to a second location. In some embodiments, the one or more items are one or more cell culture vessels. In other embodiments, the one or more items are useful for maintenance of one or more cell culture vessels and include, but are not limited to, pipettes, capillaries, liquids (e.g., cell culture medium), nutrients, and other materials. In certain embodiments, the transfer device may transfer one or more items to or from multiple locations in an incubator. For example, a transfer device may be used to move a pipette to a maintenance location in an internal chamber for maintenance of one or more cell culture vessels. In some embodiments, an incubator includes more than one transfer device for moving one or more items (e.g., two or more separate transfer devices for transferring items between and within chambers).

A transfer device may include one or more elements such as valves (e.g., electromagnetic or pneumatic valves), gears, motors (e.g., electrical or stepper motors), stages (e.g., xy or xyz stages), pistons, brakes, cables, ball-screw assemblies, rack-and-pinion arrangements, grippers, arms, pivot points, joints, translational elements, or other mechanical or electrical elements. In some embodiments, a transfer device may include one or more robotic elements. For example, a transfer device may include a robotic arm capable of gripping, lifting, pushing, grabbing, sliding, rotating, translating, releasing, raising, lowering, and/or tilting one or more items (e.g., pipettes). In preferred embodiments, the transfer device selectively and releasably grips one or more pipettes. In certain embodiments, a transfer device may include an arm coupled to a mechanical gripper. For example, an arm may include a mechanical gripper at or near one end for releasably gripping a pipette and be securely coupled to a surface or element of the incubator at or near the other end.

In some embodiments, a robotic arm includes a pivot point where the mechanical gripper couples to the arm and one or more pivot and/or translational joints along the arm to permit flexible rotation and translation of a portion of the arm. In this manner, a robotic arm may access one or more items (e.g., pipettes) at different horizontal and vertical positions within an incubator (e.g., within a storage array in an internal chamber).

As used herein, a "cell culture vessel transfer device" refers to a device that can transfer one or more cell culture vessels from a first location to a second location. In certain embodiments, the transfer device may transfer one or more items to or from multiple locations in an incubator. For example, a cell culture vessel transfer device may be used to move a cell culture vessel from a transfer chamber to an internal chamber, and/or from a storage location to an imaging location. In some embodiments, an incubator includes more than one transfer device for moving one or more items (e.g., separate means for transferring items between and within chambers). A cell culture vessel transfer device may include one or more elements such as valves (e.g., electromagnetic or pneumatic valves), gears, motors (e.g., electrical or stepper motors), stages (e.g., xy or xyz stages), pistons, brakes, cables, ball-screw assemblies, rack-and-pinion arrangements, grippers, arms, pivot points, joints, translational elements, or other mechanical or electrical elements. In some embodiments, a cell culture vessel transfer device may include one or more robotic elements. For example, a cell culture vessel transfer device may include a robotic arm capable of gripping, lifting, pushing, grabbing, sliding, rotating, translating, releasing, raising, lowering, and/or tilting one or more cell culture vessels. In preferred embodiments, the cell culture vessel transfer device selectively and releasably grips one or more cell culture vessels. In certain embodiments, a cell culture vessel transfer device may include an arm coupled to a mechanical gripper. For example, an arm may include a mechanical gripper at or near one end for releasably gripping a cell culture vessel and be securely coupled to a surface or element of the incubator at or near the other end. In some embodiments, a robotic arm includes a pivot point where the mechanical gripper couples to the arm and one or more pivot and/or translational joints along the arm to permit flexible rotation and translation of a portion of the arm. In this manner, a robotic arm may access one or more cell culture vessels at different horizontal and vertical positions within an incubator (e.g., within a storage array in an internal chamber).

In some embodiments, a transfer device includes a robotic arm. In some embodiments, the robotic arm includes a platform within an incubator cabinet that may move along a rail or conveyor running in various directions along an inner surface (e.g., inner wall, base, etc.) of incubator cabinet. In some embodiments, an incubator cabinet may be configured with more than one (e.g., 2, 3, 4, or 5, or more) robotic arms to increase the throughput of the instrument and to provide redundancy in the event that one of the robotic arms fail.

In some embodiments, a transfer device further can include a gripper assembly coupled to a robotic arm. In some embodiments, the gripper assembly includes one or more grippers mounted on the end or near the end of the robotic arm, each gripper including two or more (e.g., 3, 4, 5, or more) gripper fingers. In some embodiments, each of the gripper fingers of the robotic arm has a groove, friction plate, rubber pad, or other gripping surface. The gripping surface can allow the fingers to grip and transport various types of containers (e.g., culture vessels) within the cabinets. In some embodiments, the robotic arm may have an absolute encoder either coupled to the gripper assembly, the platform, or a separate absolute encoder for each of the gripper assembly the platform to determine whether the robotic arm is in a position where it may be safely homed (e.g., returned to a resting or storage configuration and/or location or origin of an operational coordinate system) without hitting an obstruction.

In some embodiments, because it may be desirable in certain situations for the reach of the robotic arm not to extend to some areas of the incubator cabinet, the robotic arm may instead reach these locations by inserting a container into or removing a container from a shuttle or conveyor belt located, for example on the incubator cabinet floor or other surface that moves along an axis (e.g., x-axis, y-axis) and provides access to at least some of those locations to which the robotic arm cannot reach.

In some embodiments, an incubator cabinet is designed to be used in conjunction with an external assay or laboratory automation system. For example, in some embodiments, the incubator cabinet may have a door having an opening large enough to allow the gripper arm to pivot outside of the incubator cabinet with a sufficient reach for the fingers to transport culture vessels or other containers or components between a transport line of the laboratory automation system and the incubator cabinet or the external assay components and the incubator cabinet.

In some embodiments, a robotic arm is designed to carry, among other things, culture vessels, in which case movements of the robotic arm are controlled to prevent jerking or accelerations of such vessels or other movements which may cause the spilling of samples from the vessels. In some embodiments, a robotic arm is designed to carry, among other things, culture vessels, in which case movements of the robotic arm are controlled to prevent movement of such vessels in ways which cause newly plated cells to congregate/concentrate in specific areas of the culture vessel.

In some embodiments, because a robotic arm transports vessels or other containers between specific positions in the incubator cabinet, the robotic arm or other components of the incubator can be designed to track precisely where the vessels or other containers are located. In some case, in an incubator cabinet with which a robotic arm may be used, there are likely to be areas, such as where other components of the incubator cabinet or walls of the incubator cabinet are located, and thus where certain movements of the robotic arm may be limited. In these cases, a homing mechanism can be used for each of various motors of the arms (e.g., x-motor, theta-motor and z-motor) to properly position the robotic arm to a known location after it is powered up or if a robotic arm collides with another object before resuming operation.

In some embodiments, an uninterruptible power supply ("UPS") is attached to or within the incubator cabinet, or contained with it, to allow for an orderly shut-down of incubator operations, including saving of various automation and sample information and the completion of any transport or transfer process that is underway (e.g., the transport of a container or vessel that is being carried by the robotic arm to its destination). The operator may be alerted to unauthorized opening of the incubator by an audible signal, a visual signal, an electronic signal (e.g., an email or a text message), or in some other manner. In some embodiments, a sensor or other feature is provided to detect when one or more doors of an incubator are opened (e.g., when an incubator cabinet door, such as an external or internal door, is opened). Such features are useful because they allow operators to keep track of or be warned of any unscheduled or unauthorized openings of the incubator (e.g., the incubator cabinet) that could jeopardize sterility, spoil a production, compromise an assay or experiment, etc. In some embodiments, a radiofrequency beacon or other signal source is located within the incubator (e.g., within the incubator cabinet) that can be used to determine the location of one or more devices within the incubator cabinet (e.g., devices having sensors that can detect the signal and use it to determine their location). In some embodiments, the devices could have signal sources and the sensor(s) could be located within one or more of the chambers of an incubator cabinet (e.g., located on an internal surface of an internal chamber).

In some embodiments, light signals or lasers (e.g., a grid of laser signals) can be used to determine the location of one or more devices or components within the incubator cabinet. Such information can be communicated, e.g., wired or wirelessly, to an external computer or monitoring station. The information can be used to control operation of a transfer device, e.g., a robotic arm, within the incubator cabinet to ensure that the transfer device can grab, manipulate or maneuver devices or items appropriately within the incubator cabinet.

In some embodiments, before containers or vessels are brought into an incubator cabinet, a user can select an automation system protocol based on the particular containers, vessels, ingredients, or cells that are being inserted into the incubator cabinet. Relevant information related to the incubator and/or one or more incubator components, and the cells being grown can be entered into a data system. For example, one or more identifiers such as barcodes (e.g., 1D or 2D barcodes) can be placed on the container or vessel and other significant information, such as, the type of container, the contents of the container, what assays or manipulations are to be performed on the sample in the container can be specified. In some embodiments, information related to the incubator system and/or cells can be contained in one or more barcodes, on a separate data system, or a combination thereof. The user may also enter information that identifies the dimensionality (e.g., height, diameter) of the vessel or other container, or the system itself may determine measure the height of the vessel or other container. Using this information, the robotic arm may be requested to transport a particular container, such as when an analytical module is ready to perform an assay or other manipulation on cells grown in the vessels or has completed performing an assay or manipulation.

Computer and Control Equipment

The incubators provided herein include several components, including sensors, environmental control systems, robotics, etc. which may operate together at the direction of a computer, processor, microcontroller or other controller. The components may include, for example, a transfer device (e.g., robotic arm), a liquid handling devices, a delivery system for delivering culture vessels, or other components to or from the incubator cabinet, an environmental control system for controlling the temperature and other environmental aspects of the incubator cabinet, a door operation system, an imaging or detection system, and a cell culture assay system.

In some cases, operations such as controlling operations of a cell culture incubator and/or components provided therein or interfacing therewith may be implemented using hardware, software or a combination thereof. When implemented in software, the software code can be executed on any suitable processor or collection of processors, whether provided in a single component or distributed among multiple components. Such processors may be implemented as integrated circuits, with one or more processors in an integrated circuit component. A processor may be implemented using circuitry in any suitable format.

A computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable, mobile or fixed electronic device, including the incubator itself.

In some cases, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. In other examples, a computer may receive input information through speech recognition or in other audible format, through visible gestures, through haptic input (e.g., including vibrations, tactile and/or other forces), or any combination thereof.

One or more computers may be interconnected by one or more networks in any suitable form, including as a local area network or a wide area network, such as an enterprise network or the Internet. Such networks may be based on any suitable technology and may operate according to any suitable protocol and may include wireless networks, wired networks, or fiber optic networks.

The various methods or processes outlined herein may be coded as software that is executable on one or more processors that employ any one of a variety of operating systems or platforms. Such software may be written using any of a number of suitable programming languages and/or programming or scripting tools, and may be compiled as executable machine language code or intermediate code that is executed on a framework or virtual machine.

One or more algorithms for controlling methods or processes provided herein may be embodied as a readable storage medium (or multiple readable media) (e.g., a computer memory, one or more floppy discs, compact discs (CD), optical discs, digital video disks (DVD), magnetic tapes, flash memories, circuit configurations in Field Programmable Gate Arrays or other semiconductor devices, or other tangible storage medium) encoded with one or more programs that, when executed on one or more computers or other processors, perform methods that implement the various methods or processes described herein.

In some embodiments, a computer readable storage medium may retain information for a sufficient time to provide computer-executable instructions in a non-transitory form. Such a computer readable storage medium or media can be transportable, such that the program or programs stored thereon can be loaded onto one or more different computers or other processors to implement various aspects of the methods or processes described herein. As used herein, the term "computer-readable storage medium" encompasses only a computer-readable medium that can be considered to be a manufacture (e.g., article of manufacture) or a machine. Alternatively or additionally, methods or processes described herein may be embodied as a computer readable medium other than a computer-readable storage medium, such as a propagating signal.

The terms "program" or "software" are used herein in a generic sense to refer to any type of code or set of executable instructions that can be employed to program a computer or other processor to implement various aspects of the methods or processes described herein. Additionally, it should be appreciated that according to one aspect of this embodiment, one or more programs that when executed perform a method or process described herein need not reside on a single computer or processor, but may be distributed in a modular fashion amongst a number of different computers or processors to implement various procedures or operations.

Executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

Also, data structures may be stored in computer-readable media in any suitable form. Non-limiting examples of data storage include structured, unstructured, localized, distributed, short-term and/or long term storage. Non-limiting examples of protocols that can be used for communicating data include proprietary and/or industry standard protocols (e.g., HTTP, HTML, XML, JSON, SQL, web services, text, spreadsheets, etc., or any combination thereof). For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags, or other mechanisms that establish relationship between data elements.

In some embodiments, information related to the operation of the incubator (e.g., temperature, humidity, gas composition, images, cell culture conditions, etc., or any combination thereof) can be obtained from one or more sensors associated with the incubator (e.g., located within the incubator cabinet, or located within the incubator but outside the incubator cabinet), and can be stored in computer-readable media to provide information about conditions during a cell culture incubation. In some embodiments, the readable media comprises a database. In some embodiments, said database contains data from a single incubator. In some embodiments, said database contains data from a plurality of incubators. In some embodiments, data is stored in a manner that makes it tamper-proof. In some embodiments, all data generated by the instrument (e.g., an incubator) is stored. In some embodiments, a subset of data is stored.

In some embodiments, the component (e.g., a computer) controls various processes performed inside the incubator. For example, a computer may direct control equipment (e.g., a manipulator, an imager, a fluid handling system, etc.). In some embodiments, the computer controls imaging of cell cultures, picking of cells, weeding of cells (e.g., removal of cell clumps), monitoring of cell culture conditions, adjustment of cell culture conditions, tracking of cell culture vessel movement within the incubator, and/or scheduling of any of the foregoing processes.

Cell Assays

In certain embodiments, incubators provided herein are configured to permit one or more assays to be performed within an incubator cabinet or within a chamber operably connected to an incubator cabinet, e.g., a separate assay chamber that is part of the incubator. In some embodiments, incubators provided herein are configured to permit performance of a cell counting assay, a replication labeling assay, a cell membrane integrity assay, a cellular ATP-based viability assay, a mitochondrial reductase activity assay, a caspase activity assay, an Annexin V staining assay, a DNA content assay, a DNA degradation assay, a nuclear fragmentation assay, or a combination thereof. Other exemplary assays include BrdU, EdU, or H3-thymidine incorporation assays; DNA content assays using a nucleic acid dye, such as Hoechst Dye, DAPI, actinomycin D, 7-aminoactinomycin D, or propidium iodide; cellular metabolism assays such as AlamarBlue, MTT, XTT, and CellTitre Glo; nuclear fragmentation assays; cytoplasmic histone associated DNA fragmentation assays; PARP cleavage assays; and, TUNEL staining assays.

In some embodiments, incubators provided herein are configured to permit digital identification and marking of cells. For example, a cell or cells may be cultured in an incubator described herein and imaged via fluorescent microscopy to digitally mark (e.g., via a computer having imaging software that is connected to the incubator) a cell or cells (e.g., a cell population) of interest (e.g., cells positive for fluorescence). The location of the marked cells can be stored on the computer's memory and accessed at a later time point. The digital marking of cell populations may permit marked cells to be subsequently viewed or manipulated. The subsequent viewing, and/or manipulating may be performed at the same location (e.g., an imaging location) at which the cells were digitally marked, or at a location remote from the location at which the cells were digitally marked (e.g., a manipulation location that is not the imaging location). In some cases, the digital marking of a cell or cells may be facilitated by alignment of the cell culture vessel housing said cells to the imager via one or more fiducial marks. In some embodiments, an incubator as described herein comprises a plurality of workstations (e.g., 1, or 2, or 3, or 4, or 5, or more workstations), wherein each workstation is configured to permit digital identification and marking of cells.

In certain embodiments, incubators provided herein are configured to permit high-throughput screening (HTS) within an incubator cabinet. In some embodiments, HTS refers to testing of up to, and including, 100,000 compounds per day. In some embodiments, screening assays may be carried out in a multi-well format, for example, a 96-well, 384-well format, or 1,536-well format, and can be performed using automated protocols. In such high throughput assays, it is possible to screen several thousand different compounds or compositions in a single day. In particular, each well of a microtiter plate can be used to run a separate assay against a selected test compound, or, if concentration or incubation time effects are to be observed, a plurality of wells can contain test samples of a single compound. It is possible to assay many plates per day; assay screens for up to about 6,000, 20,000, 50,000, or more than 100,000 different compounds are possible using the assays. Typically, HTS implementations of the assays disclosed herein involve the use of automation. In some embodiments, an integrated robot system that includes one or more robotic arms transports assay microplates between multiple assay stations for compound, cell and/or reagent addition, mixing, incubation, and finally readout or detection. In some aspects, an HTS assay may include preparing, incubating, and analyzing many plates simultaneously, further speeding the data-collection process.

In some embodiments, assays can include test cells, control cells, and one or more test compounds, e.g., 10, 100, 1000, 10,000, or more test compounds. The cells and test agents can be arranged in one or more vessels in a manner suitable for assessing effect of the test compound(s) on the cells. These assays can be performed within one or more incubator cabinets of one or more incubators described herein. Typically, the vessels contain a suitable tissue culture medium, and the test compounds are present in the tissue culture medium and may be delivered to the culture medium within an incubator cabinet of an incubator provided herein in an automated fashion. A medium appropriate for culturing a particular cell type can be selected for use. In some embodiments, a medium is free or essentially free of serum or tissue extracts, while in other embodiments such a component is present. In some embodiments, cells are cultured on a plastic or glass surface.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, e.g., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A);

in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, e.g., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (e.g. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, e.g., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A cell culture incubator comprising:
an incubator cabinet comprising an internal chamber for incubation of cells in one or more cell culture vessels, a holographic imager comprising a first imaging location, said holographic imager configured for imaging said cells within said internal chamber when said one or more cell culture vessels are at said first imaging location;

a storage location within said internal chamber for storing said one or more cell culture vessels;

a cell culture vessel transfer device for moving said one or more cell culture vessels from said first imaging location to said storage location or from said storage location to said first imaging location; and a device controller for controlling the cell culture transfer device and the imager and configured to process image information and produce control signals based on the processed image information when environmental conditions have changed, wherein the controller is configured to obtain a three dimensional stack of images of cells during culture for analysis, wherein the images in the three dimensional stack of images are at different focal planes wherein the controller is configured to create a complete image by stitching sub-images together from different focal planes.

2. The incubator of claim 1, wherein the controller is configured to use a passive autofocus to select a focal plane with no mechanical movement.

3. A cell culture incubator comprising:

an incubator cabinet comprising an internal chamber for incubation of cells in one or more cell culture vessels, a phase-contrast imager comprising a first imaging location, said phase-contrast imager configured for imaging said cells within said internal chamber when said one or more cell culture vessels are at said first imaging location;

a storage location within said internal chamber for storing said one or more cell culture vessels;

a cell culture vessel transfer device for moving said one or more cell culture vessels from said first imaging location to said storage location or from said storage location to said first imaging location; and a device controller for controlling the cell culture transfer device and the imager and configured to process image information and produce control signals based on the processed image information when environmental conditions have changed, wherein the controller is configured to obtain a three dimensional stack of images of cells during culture for analysis, wherein the images in the three dimensional stack of images are at different focal planes wherein the controller is configured to create a complete image by stitching sub-images together from different focal planes.

4. The incubator of claim 3, wherein the controller is configured to use a passive autofocus to select a focal plane with no mechanical movement.

5. The incubator of claim 3, wherein the controller is configured to analyze shape variations between cells in suspension to compensate for defocus effects resulting from movement of cells in suspension.

6. The incubator of any claim 3, wherein the controller is configured to record an interference pattern to reconstruct an image for analysis with a numerical reconstruction algorithm.

7. The incubator of claim 3, wherein cell culture vessels include bar codes encoding bar code data and the incubator includes a bar code reader for reading the bar codes and wherein the controller receives the bar code data to select a system protocol based at least in part on the bar code data to determine operations to be performed on cells in the corresponding cell culture vessel.

8. The incubator of claim 3, wherein the controller is configured to digitize an interference pattern as a two-dimensional array of integers with an 8-bit or higher grayscale resolution.

* * * * *